(12) United States Patent
Butz et al.

(10) Patent No.: US 9,173,479 B2
(45) Date of Patent: Nov. 3, 2015

(54) DEVICE FOR CLEANING THE MOUTH OR TEETH

(71) Applicant: Interbros GmbH, Schoenau (DE)

(72) Inventors: Juergen Butz, Schoenau (DE); Hannes Hauser, Steinen (DE); Gerhard Poetsch, Freiburg (DE)

(73) Assignee: Interbros GmbH, Schönau (DE)

( * ) Notice: Subject to any disclaimer, the term of this patent is extended or adjusted under 35 U.S.C. 154(b) by 0 days.

(21) Appl. No.: 14/727,894

(22) Filed: Jun. 2, 2015

(65) Prior Publication Data

US 2015/0257523 A1 Sep. 17, 2015

Related U.S. Application Data

(63) Continuation of application No. 13/984,298, filed as application No. PCT/EP2012/000636 on Feb. 14, 2012, now abandoned.

(30) Foreign Application Priority Data

Feb. 16, 2011 (DE) .......................... 10 2011 011 323

(51) Int. Cl.

| A46B 15/00 | (2006.01) |
|---|---|
| A46B 5/02 | (2006.01) |
| A46B 9/00 | (2006.01) |
| A61C 15/02 | (2006.01) |
| B25G 1/10 | (2006.01) |
| B43K 23/008 | (2006.01) |

(52) U.S. Cl.
CPC ............. *A46B 15/0071* (2013.01); *A46B 5/021* (2013.01); *A46B 5/026* (2013.01); *A46B 9/005* (2013.01); *A46B 15/0081* (2013.01); *A61C 15/02* (2013.01); *B25G 1/102* (2013.01); *B43K 23/008* (2013.01)

(58) Field of Classification Search
CPC ........... A46B 15/0071; A46B 15/0081; A46B 5/021; A46B 5/026; A46B 9/005; A61C 15/00; A61C 15/02; A61C 17/24; B25G 1/102; B43K 23/008
See application file for complete search history.

(56) References Cited

U.S. PATENT DOCUMENTS

| 5,778,475 | A | * | 7/1998 | Garcia | ............................. | 15/111 |
|---|---|---|---|---|---|---|
| 5,915,433 | A | * | 6/1999 | Hybler | ............................. | 15/111 |
| 7,182,542 | B2 | * | 2/2007 | Hohlbein | ....................... | 401/268 |
| 2006/0052805 | A1 | * | 3/2006 | Cwik | ............................. | 606/161 |
| 2006/0165473 | A1 | * | 7/2006 | Hohlbein | ....................... | 401/132 |
| 2007/0163064 | A1 | * | 7/2007 | Wong et al. | .................. | 15/143.1 |

* cited by examiner

Primary Examiner — Robyn Doan
(74) Attorney, Agent, or Firm — Paul Vincent

(57) ABSTRACT

A device for cleaning the mouth or teeth has a rod-shaped support, on one axial end of which an interdental cleaner made of a flexible plastic is arranged. A brush-like cleaning part made of a flexible plastic, and having a plurality of protruding cleaning elements, is arranged at the opposite axial end of the rod-shaped support. In addition, the rod-shaped support has a grip portion made of a flexible plastic and arranged preferably in the central area of the axial length of the rod-shaped support. Provision is made that the grip portion is connected, via at least one connecting portion, to the interdental cleaner and/or to the brush-like cleaning part so as to form a one-piece structure.

13 Claims, 6 Drawing Sheets

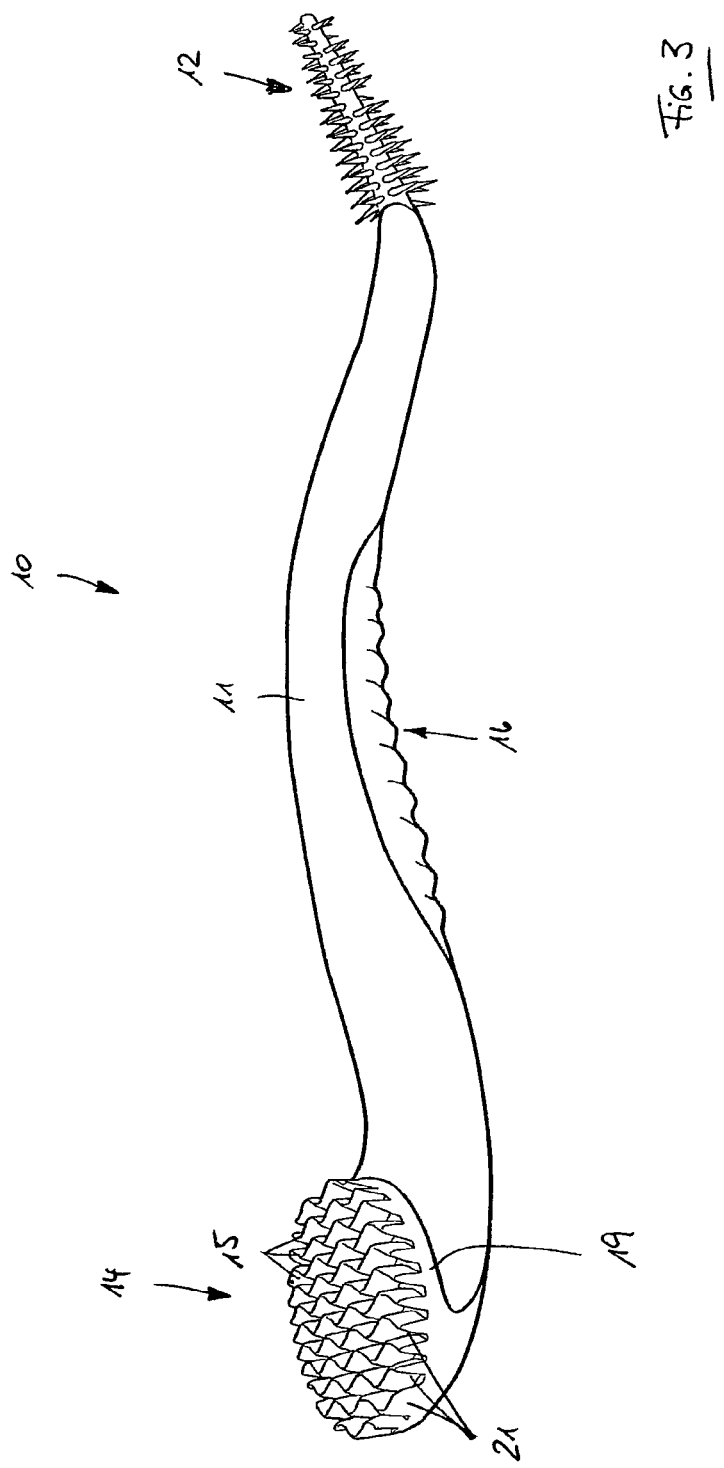

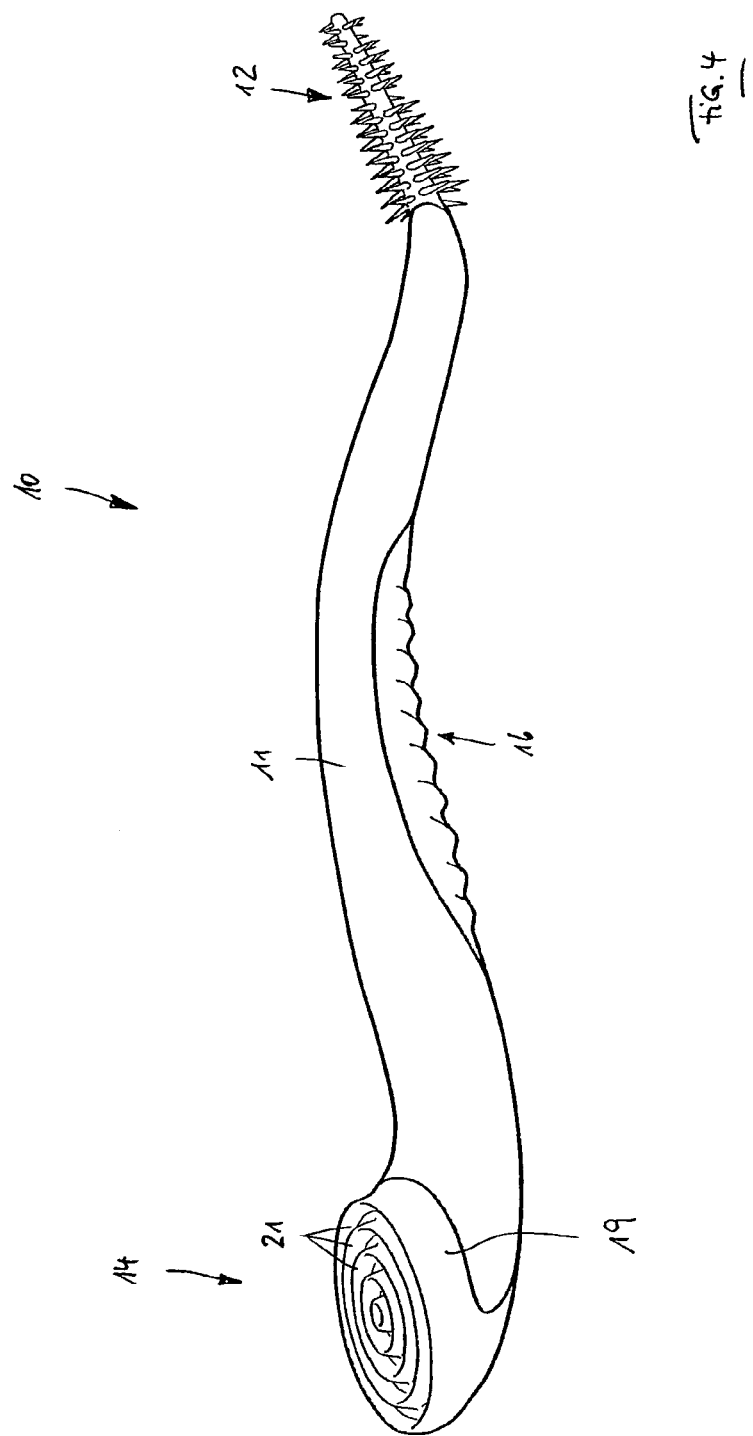

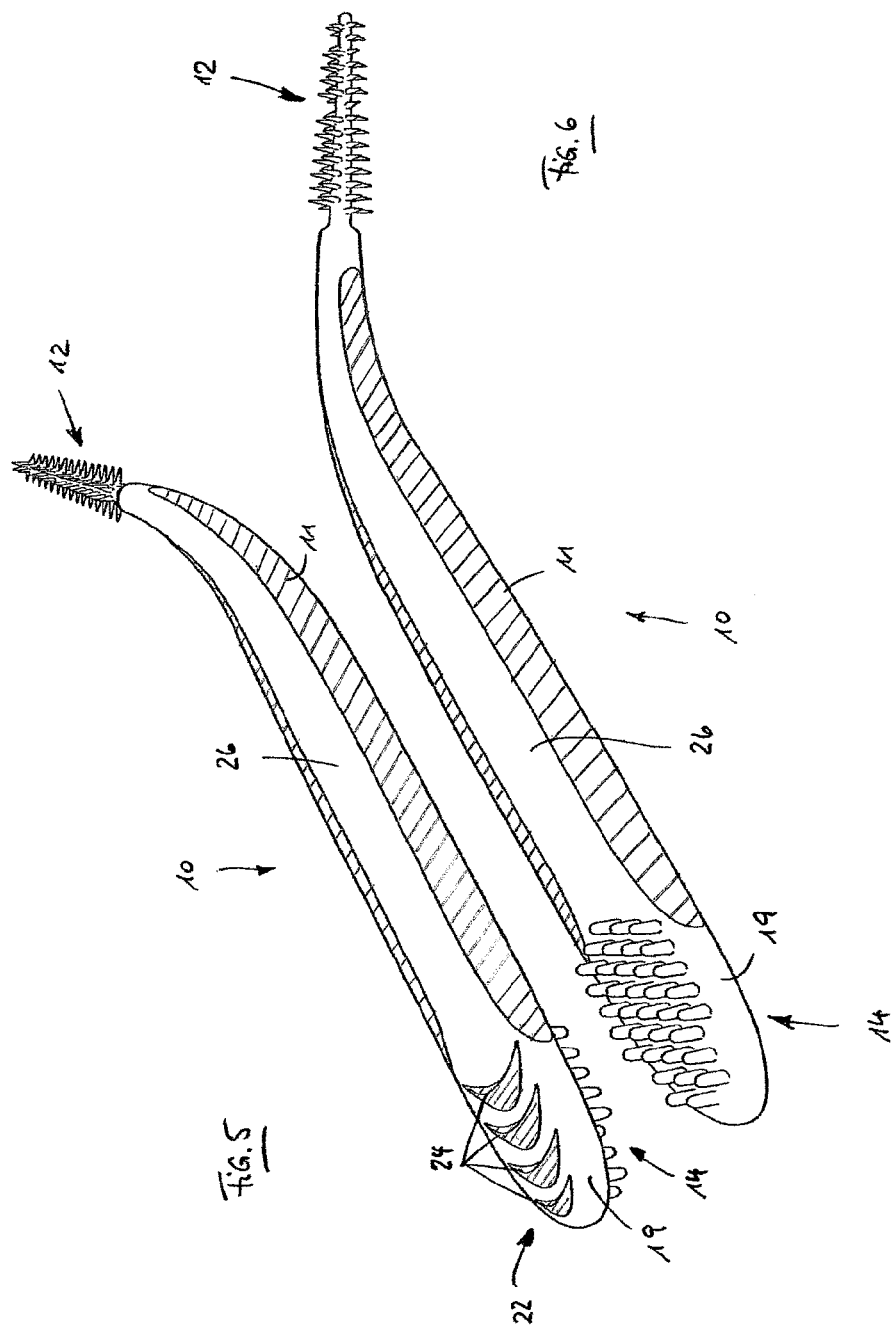

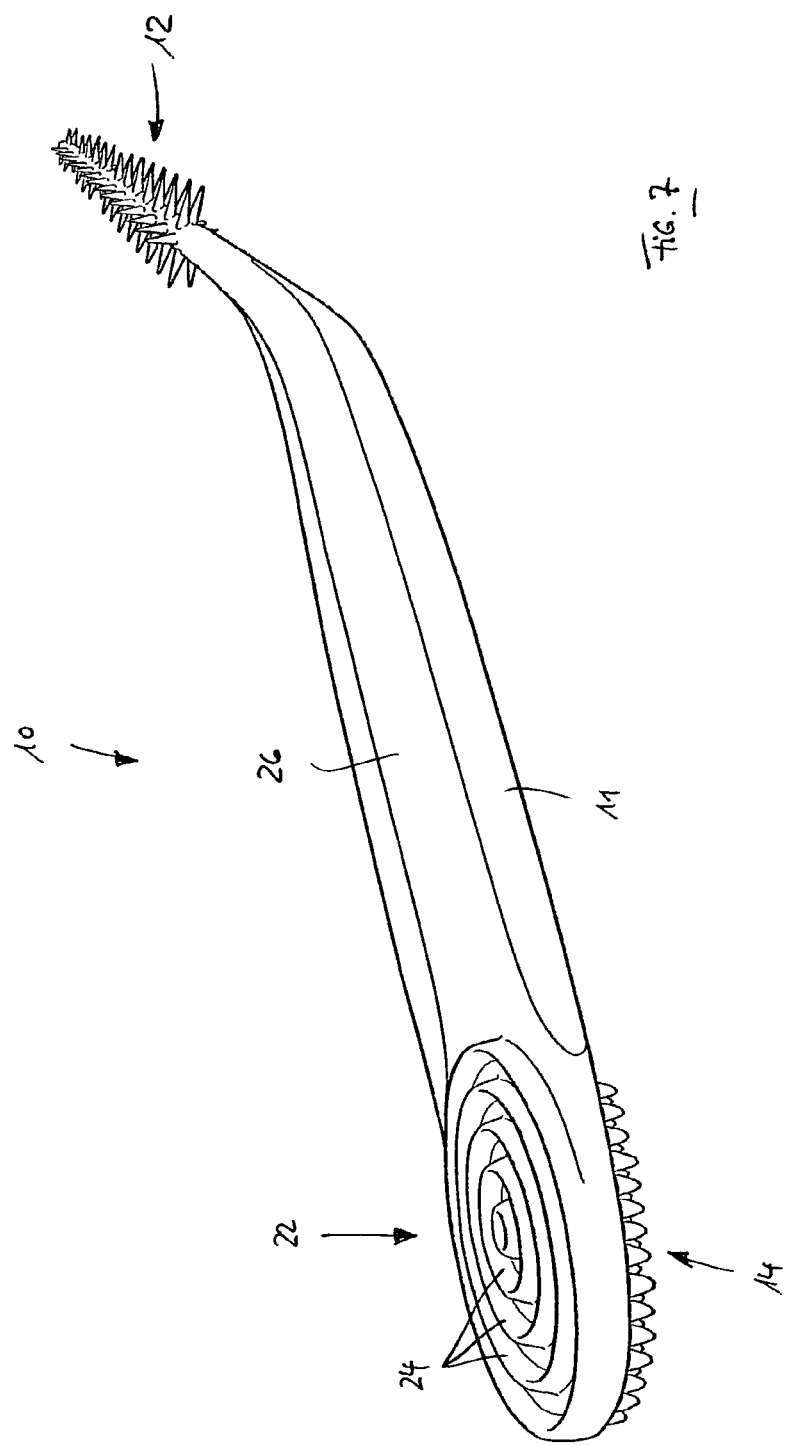

DEVICE FOR CLEANING THE MOUTH OR TEETH

This application is a continuation of Ser. No. 13/984,298 filed Oct. 8, 2013 as the national stage of PCT/EP2012/00636 filed Feb. 14, 2012 and also claims Paris convention priority from DE 10 2011 011 323.1 filed Feb. 16, 2011, the entire disclosures of which are hereby incorporated by reference.

BACKGROUND OF THE INVENTION

The invention relates to a device for cleaning the mouth or teeth with a rod-shaped support, on one axial end of which an interdental cleaner made of a flexible plastic is arranged, and on the opposite axial end of which a brush-like cleaning part made of a flexible plastic and having a plurality of protruding cleaning elements is arranged, wherein the rod-shaped support has a grip portion made of a flexible plastic.

Such a device for cleaning the mouth or teeth is known from EP 2 179 677 A1. It consists of a rod-shaped support made of a dimensionally stable plastic, on the front axial end of which an interdental cleaner shaped like a tooth pick is arranged, which is made of a flexible plastic. On its opposite axial end, the device for cleaning the mouth or teeth has a brush-like cleaning part with bristles, which is also made of a flexible plastic. A grip portion made of a flexible plastic is constituted on the rod-shaped support between interdental cleaner and the cleaning part, allowing the user to grip the device securely for cleaning the mouth or teeth.

An essential aspect of the functionality of the device for cleaning the mouth or teeth is that a fixed and permanent connection exists between the flexible plastic of the interdental cleaner, the cleaning part and the grip portion with the rod-shaped support. Although this can be achieved with undercuts in the rod-shaped support, this makes the tool for manufacturing the device for cleaning the mouth or teeth complex and expensive.

The object of the invention is to manufacture a multifunctional device for cleaning the mouth or teeth of the type stated above in which a good connection between the flexible plastic of the functional regions and the rod-shaped support is provided in a simple manner.

SUMMARY OF THE INVENTION

This object is inventively achieved with a device for cleaning the mouth or teeth with the characteristics of the independent claim.

In addition to the interdental cleaner made of a flexible plastic, which is disposed at one axial end of the rod-shaped support, a brush-like cleaning part is disposed at the opposite axial end of the rod-shaped support, being also made of a flexible plastic and having a plurality of protruding cleaning elements.

Preferably, a grip portion made of a flexible plastic is also arranged in the central area of the axial length of the rod-shaped support. This helps the user grip the device for cleaning the mouth or teeth and hold it securely. In addition, the surface of the grip portion can have protruding elevations, for example, ribs or studs.

In order to increase the overall stability of the device for cleaning the mouth or teeth, according to the invention, the grip portion is connected to the interdental cleaner and/or the brush-like cleaning part by at least one preferably ridge-like connecting portion so as to form a uniform, one-piece structure. In this way the interdental cleaner or the brush-like cleaning part is prevented from becoming detached from the rod-shaped support during use because, due to the connection with the grip portion, they are held onto the rod-shaped support in an interlocking manner. In a preferred embodiment of the invention, the grip portion is connected both with the interdental cleaner and with the brush-like cleaning part via the connection ridges to form a one-piece structure. In this case, the interdental cleaner, the brush-like cleaning part and the grip portion are all made of the same flexible plastic.

The device for cleaning the mouth or teeth is manufactured in a two- or multiple component injection molding process. In a first process step, the rod-shaped support is preferably injection-molded from a dimensionally stable plastic (polypropylene (PP), polyethylene (PE), or polyethylene terephthalate (PET), wherein the plastic can be strengthened with fibers or beads. In a second process step the grip portion, the interdental cleaner and the brush-like cleaning part are preferably simultaneously injection-molded onto the rod-shaped support, wherein the grip portion, the interdental cleaner and the cleaning part can be made of, for example, a thermoplastic elastomer or silicone or EPDM (ethylene propylene diene monomer).

The interdental cleaner preferably has radially protruding, integrally molded cleaning elements. The radially protruding cleaning elements of the interdental cleaner may be brush-like fingers, studs, or ribs.

The cleaning elements of the brush-like cleaning part can be at least partially constituted by fingers integrally molded on a support part so as to form a one-piece structure. In this case a multiplicity of fingers are preferably disposed adjacently and especially aligned in parallel, each of which is connected at its lower end with the support part so as to form a one-piece structure. Both the fingers and the support part are made of a flexible plastic.

Alternatively or additionally, the cleaning elements of the brush-like cleaning part can be at least partially constituted by lamellas integrally molded on the support part so as to form a one-piece structure. The lamellas have a larger spatial stability than the fingers so that a greater cleaning force can be applied via the lamellas onto the surface to be cleaned and in particular onto the tooth surface. This is particularly the case if, in a further embodiment of the invention, each of the lamellas each has a wavy or zig-zag shape.

In a further embodiment of the invention, the lamellas can be disposed in multiple concentric circles.

The interdental cleaner constituted at one axial end of the rod-shaped support is used to clean the spaces between the teeth, whereas the brush-like cleaning part should be used to clean the teeth surfaces. In a further embodiment of the invention, a tongue scraper can be disposed on the side of the rod-shaped support facing away from the cleaning part at its same axial end. In this case, the scraper elements of the tongue scraper can be constituted by a plurality of ribs protruding from a support part.

After the user has cleaned the tooth surface with the brush-like cleaning part, he merely has to rotate the device for cleaning the mouth or teeth by 180° and can then clean the surface of the tongue with the tongue scraper. Portions of the tongue scraper may consist of a flexible plastic and, in particular, of the same flexible plastic as the interdental cleaner and/or the cleaning part and/or the grip portion. The tongue scraper can be connected with the cleaning part to form a uniform and one-piece structure, wherein especially the tongue scraper and the cleaning part use the support part as a common base for their cleaning elements or ribs.

In a preferred embodiment of the invention, the ribs of the tongue scraper can extend transversely with respect to the longitudinal direction of the rod-shaped support and are spaced one behind the other. In particular, the ribs can be curved in a sickle shape.

Alternatively, it is also possible for the ribs to be disposed in multiple concentric circles.

In a preferred embodiment of the invention, the ribs of the tongue scraper are not made from a flexible plastic but from the same material as the rod-shaped support, that is, in particular a dimensionally stable plastic. As a result, the ribs exhibit very high rigidity, which improves the scraping and scratching effect on the surface of the tongue.

In this case, the ribs are preferably connected with the rod-shaped support so as to form a uniform and one-piece structure and can be manufactured together with the latter in a two- or multiple component injection molding process in a first process step.

In a further embodiment of the invention, the material of the interdental cleaner and/or of the brush-like cleaning part and/or of the tongue scraper is provided with an additive. This additive might be, for example, a flavoring or a substance with a disinfectant effect or a substance to assist teeth cleansing. In a possible embodiment of the invention, the additive can be introduced into or is embedded in the material of the interdental cleaner and/or of the cleaning part and/or of the tongue scraper in the usual way.

In an alternative embodiment of the invention, the additive is applied all over or to individual areas of the exterior of the interdental cleaner and/or to the cleaning part and/or to the tongue scraper. This can be done, for example, by a spraying or immersion process. The main advantage over embedding the additive into the material is that different additives can be applied to the interdental cleaner and/or to the cleaning part and/or to the tongue scraper. Moreover, it is possible to apply the additive only to certain areas of the interdental cleaner and/or the cleaning part and/or the tongue scraper.

The device for cleaning the mouth or teeth described above can be manufactured and sold as an individual part. However, it is also possible to connect together a plurality of devices for cleaning the mouth or teeth by means of thin bars made of plastic so that they are disposed side by side, forming a strip of multiple devices for cleaning the mouth or teeth, from which the user can remove one device for cleaning the mouth or teeth when needed by breaking the strips.

Further details and characteristics of the invention can be seen from the following description of embodiments with reference to the drawing. The figures show:

DESCRIPTION OF THE PREFERRED EMBODIMENT

Figure 1:
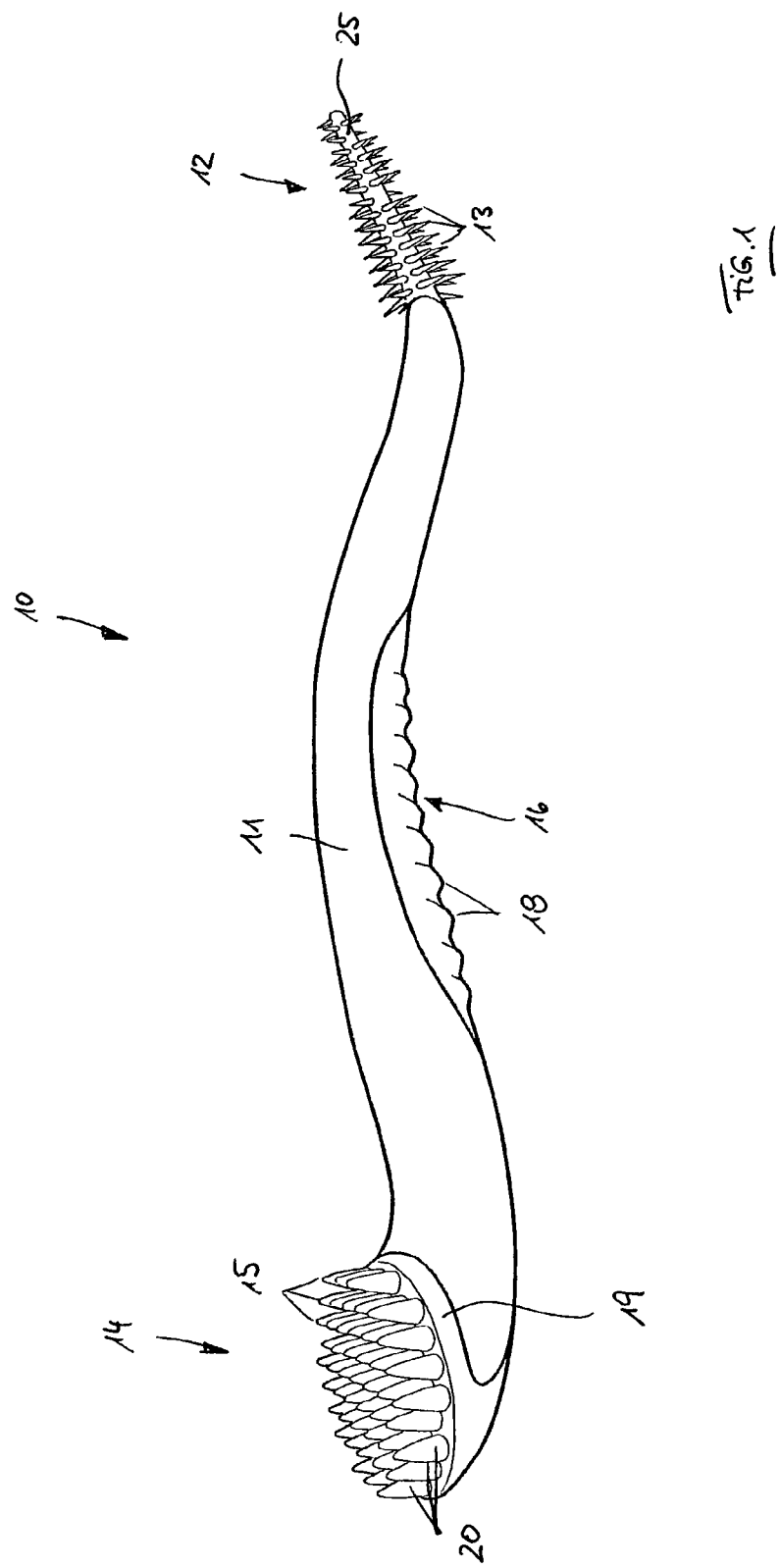
FIG. 1 A perspective side view of a device for cleaning the mouth or teeth according to the first embodiment, FIG. 2 A rear view of the device for cleaning the mouth or teeth according to FIG. 1, FIG. 3 A first variation of the device for cleaning the mouth or teeth according to FIG. 1, FIG. 4 A second variation of the device for cleaning the mouth or teeth according to FIG. 1, FIG. 5 A perspective view from above of a device for cleaning the mouth or teeth according to a second embodiment, FIG. 6 A perspective view from below of the device for cleaning the mouth or teeth according to FIG. 5, and FIG. 7 A variation of the device for cleaning the mouth or teeth according to FIG. 5.
Figure 2:
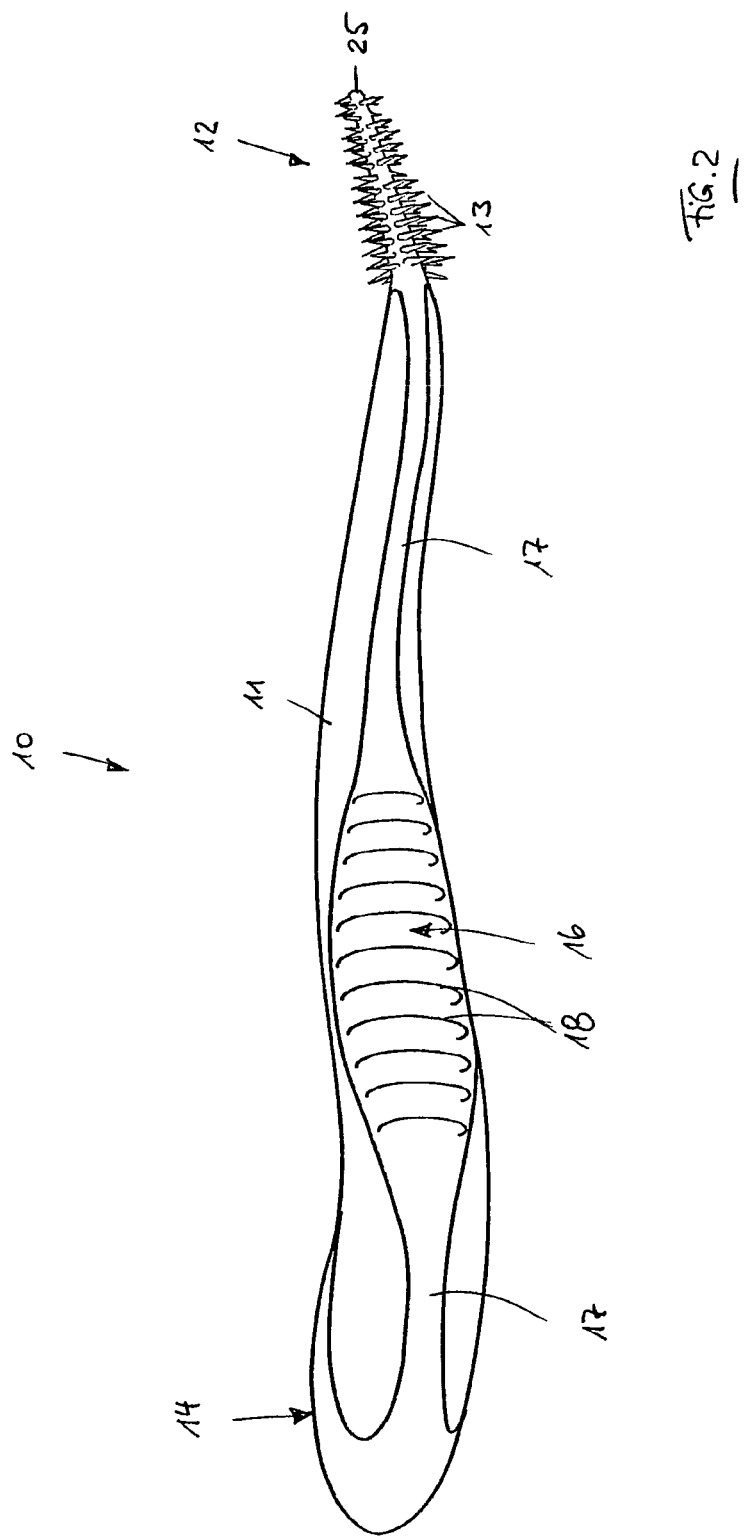

According to FIGS. 1 and 2, a device for cleaning the mouth or teeth 10 has a rod-shaped support 11, which for ergonomic reasons is slightly curved and is made of a dimensionally stable plastic, in particular reinforced or non-reinforced PP, PE, or PET. An interdental cleaner 12 made of a flexible plastic, in particular, a thermoplastic elastomer or silicone or EPDM is constituted at the right axial end of the rod-shaped support 11, according to FIG. 1. The interdental cleaner 12 has a rod-shaped or sleeve-shaped base part 25, on the outside surface of which a multiplicity of cleaning elements 13, radially protruding to the outside and shaped like brush-like fingers, are disposed. The rod-shaped base part 25 and the cleaning elements 13 are made of a flexible plastic, in particular, a thermoplastic elastomer or silicone and are preferably injection-molded onto the rod-shaped support.

According to FIG. 1, a brush-like cleaning part 14 is disposed at the opposite axial end, that is, at the left end of the rod-shaped support 11. The cleaning part 14 consists of a disk-shaped carrier part 19, which carries a multiplicity of fingers 20 on its surface, which protrude upward radially, are aligned in parallel and taper to a cone at their top end. The carrier part 19 and the fingers 20 are made of the same flexible plastic as the interdental cleaner 12.

In the central area of the rod-shaped support 11, a grip portion 16 is disposed having a multiplicity of parallel elevations in the shape of ribs 18 on its surface. The grip portion 16 is also made of the same flexible plastic as the interdental cleaner 12.

As FIG. 2 shows, both the interdental cleaner 12 and the cleaning part 14 are connected via a ridge-like connecting portion 17 made of flexible plastic with the grip portion 16, to form a uniform structure, which consequently consists completely of the flexible plastic.

FIG. 3 shows a 1st variant embodiment of the device for cleaning the mouth or teeth 10 according to FIG. 1, wherein the only difference lies in the embodiment of the cleaning elements 15 of the brush-like cleaning part 14. In the embodiment according to FIG. 3, the cleaning elements 15 are constituted in the shape of multiple parallel lamellas 21, each of which extend transversely to the longitudinal direction of the rod-shaped support 11 and run parallel with one another. Each lamella has a wavy or zig-zag shape, which lends the lamellas 21 more spatial rigidity.

FIG. 4 shoes a variant of the embodiment of the device for cleaning the mouth or teeth according to FIG. 3, wherein here the lamellas 21 of the cleaning part 14 are disposed as concentric circles.

The embodiments presented and described above perform two functions, namely at one axial end as an interdental cleaner and at their opposite axial end as a cleaning part for cleaning tooth surfaces. The devices for cleaning the mouth or teeth depicted in FIGS. 5 to 7 additionally have a third functional section.

As FIGS. 5 and 6 show, the device for cleaning the mouth or teeth 10 additionally has a tongue scraper 22 disposed on the left axial end of the rod-shaped support 11, that is, at the same axial end at which the cleaning part 14 is also disposed. The tongue scraper 22 is disposed on side of the rod-shaped support 11 facing away from the cleaning part 14 and has protruding scraping elements 24, which, in the embodiment depicted in FIG. 5, are constituted by a plurality of ribs 24 that protrude from the carrier part 19. The ribs 24 are sickle-shaped and extend transversely with respect to the longitudinal direction of the rod-shaped support and are disposed spaced one behind the other. Portions of the tongue scraper 22 region can consist of the same flexible plastic as the interdental cleaner, the cleaning part, and the grip portion with the ribs 24 of the tongue scraper 22 being made from the dimensionally stable plastic of the rod-shaped support.

According to FIG. 5, the tongue scraper 22 is connected to the interdental cleaner 12 so as to form a one-piece structure via a connecting portion 26 made of the same flexible plastic, which extends in the longitudinal direction of the rod-shaped support 11. On the opposite side of the rod-shaped support 11 (s. FIG. 6), the cleaning part 14 is also connected to the interdental cleaner 12 via a connecting portion 26 made of the flexible plastic so that the interdental cleaner 12, the cleaning part 14, and portions of the tongue scraper 22 region are combined into a one-piece structure made of the flexible plastic and held onto the rod-shaped support 11 in an interlocking manner. As is schematically indicated in the figures with cross-hatching, the ribs 24 of the tongue scraper 22 are made from the same plastic material as the rod-shaped support 11.

The rod-shaped support 11 is bent laterally at its end portion which holds the interdental cleaner 12, in order to make it easier to insert the interdental cleaner 12 into the spaces between the teeth.

FIG. 7 shows a further embodiment of a device for cleaning the mouth or teeth 10 with a three-fold function. It essentially differs from the device for cleaning the mouth or teeth 10 according to FIGS. 5 and 6 in that the ribs 24 of the tongue scraper 22 are disposed as a plurality of concentric circles. Here again, the end portion of the rod-shaped support 11 that holds the interdental cleaner is bent laterally, and the cleaning part 14 and the tongue scraper 22 together with the interdental cleaner 12 are all made from the same flexible plastic and interconnected via connecting ridges 26 made of the same material, which extend along both sides of the rod-shaped support 11.

We claim:

1. A device for cleaning the mouth or teeth, the device comprising:
    a rod-shaped support having a first and a second end, said rod-shaped support being made of a dimensionally stable plastic;
    an interdental cleaner made of a flexible plastic, said interdental cleaner disposed at said first end of said rod-shaped support;
    a brush-like cleaning part disposed at said second end of said rod-shaped support, said brush-like cleaning part being made of said flexible plastic and having a plurality of protruding cleaning elements;
    a grip portion disposed on said rod-shaped support, said grip portion being made of said flexible plastic, wherein said grip portion is integral with said interdental cleaner and said brush-like cleaning part, thereby constituting a first one-piece structure made of said flexible plastic; and
    a tongue scraper having protruding scraping elements, said tongue scraper being disposed on a first carrier part at said second end of said rod-shaped support to face away from said cleaning part, wherein said scraping elements are constituted by a plurality of ribs protruding from said first carrier part, said ribs being made of said dimensionally stable plastic, wherein said ribs are integral with said rod-shaped support, thereby constituting a second one-piece structure made of said dimensionally stable plastic and connected to said first one-piece structure made of said flexible plastic.

2. The device for cleaning the mouth or teeth of claim 1, wherein said ribs extend transversely with respect to a longitudinal direction of said rod-shaped support and are spaced one behind another.

3. The device for cleaning the mouth or teeth of claim 1, wherein said ribs are disposed in multiple concentric circles.

4. The device for cleaning the mouth or teeth of claim 1, wherein said grip portion is disposed in a central area of an axial length of said rod-shaped support.

5. The device for cleaning the mouth or teeth of claim 1, wherein the interdental cleaner has radially protruding integrally molded cleaning elements so as to form a one-piece unit.

6. The device for cleaning the mouth or teeth of claim 1, wherein said cleaning elements of said cleaning part are at least partially constituted by fingers integrally molded on a second carrier part so as to form a one-piece structure.

7. The device for cleaning the mouth or teeth of claim 1, wherein said cleaning elements of said cleaning part are at least partially constituted by lamellas integrally molded on a second carrier part so as to form a one-piece structure.

8. The device for cleaning the mouth or teeth of claim 7, wherein said lamellas each have a wavy or zig-zag shape.

9. The device for cleaning the mouth or teeth of claim 8, wherein said lamellas are disposed in multiple concentric circles.

10. The device for cleaning the mouth or teeth of claim 1, wherein a material of said interdental cleaner, of said cleaning part and/or of said tongue scraper is provided with an additive.

11. The device for cleaning the mouth or teeth of claim 10, wherein said additive is a flavoring, a substance with a disinfectant effect or a substance to assist teeth cleansing.

12. The device for cleaning the mouth or teeth of claim 10, wherein said additive is applied to an exterior of said interdental cleaner, of said cleaning part and/or of said tongue scraper.

13. The device for cleaning the mouth or teeth of claim 10, wherein said additive is embedded in a material of said interdental cleaner, of said cleaning part and/or of said tongue scraper.

* * * * *